United States Patent [19]
Shiono et al.

[11] Patent Number: 5,566,673
[45] Date of Patent: Oct. 22, 1996

[54] APPARATUS FOR MEASURING BRAIN ACTIVITY

[75] Inventors: Satoru Shiono, Hyogo; Manabu Tanifuji, Fukui, both of Japan

[73] Assignee: Mitsubishi Denki Kabushiki Kaisha, Tokyo, Japan

[21] Appl. No.: 457,373

[22] Filed: Jun. 1, 1995

[30] Foreign Application Priority Data

Aug. 3, 1994 [JP] Japan .................................... 6-182334

[51] Int. Cl.⁶ ........................................................ A61B 5/00
[52] U.S. Cl. ........................ 128/653.1; 128/630; 128/664; 128/665
[58] Field of Search ..................... 128/630, 633, 128/663.01, 653, 654, 664, 665, 731

[56] References Cited

U.S. PATENT DOCUMENTS 4,953,968  9/1990  Sherwin et al. ................... 128/731 X
5,052,401  10/1991  Sherwin ............................. 128/731 X
5,198,977  3/1993  Salb .
5,438,989  8/1995  Hochman et al. ................. 128/664 X

FOREIGN PATENT DOCUMENTS 619187  11/1990  Japan .

Primary Examiner—Angela D. Sykes
Assistant Examiner—Stephen D. Huang
Attorney, Agent, or Firm—Wolf, Greenfield & Sacks, P.C.

[57] ABSTRACT

In a brain activity measuring apparatus, the reflected light from the brain surface is conducted by way of an objective lens and focusing lens and split into two beams by a beam splitter. The light beams are conducted through respective band-pass filters having different transmission wavelengths, and received by CCD cameras in which images are formed from the filtered light beams. The CCD cameras produce signals of the images, and a differential amplifier subtracts one image signal from the other thereby to remove a background noise component. The apparatus is free from noises caused by mechanical vibration, and the resulting differential signal exhibits the brain activity accurately.

33 Claims, 10 Drawing Sheets

APPARATUS FOR MEASURING BRAIN ACTIVITY

BACKGROUND OF THE INVENTION

1. Field of the Invention

The present invention relates to a brain activity measuring apparatus for measuring the nervous activity from above the brain surface for the purpose of studying the information processing mechanism of the brain or for the purpose of the anatomical localization at the brain surgery.

2. Description of the Prior Art

FIG. 1 shows the arrangement of the conventional brain activity measuring apparatus disclosed in Japanese Patent Publication No. Hei 5-237118 (issued on Sep. 17, 1993) which is derived from U.S. Pat. No. 5,198,977 (patented on Mar. 30, 1993). In the figure, reference numeral 1 denotes the brain surface of an animal including human; 2, a light source which produces and projects a ray of light onto the brain surface 1; and 3, a filter positioner having a revolving section 3a, on which optical band-pass filters 4 and 5 which transmit light components of different frequency bands are fitted. Accordingly, the light components having two kinds of wavelengths are projected alternately onto the brain surface 1 as the revolving section 3a of the filter positioner 3 turns. The filters 4 and 5 transmit the light components of wavelengths 586 nm and 569 nm, respectively.

Indicated by 6 is a lens barrel; 7, an objective lens fitted in the lens barrel 7; and 8, a focusing lens which focuses the reflected light from the brain surface 1.

Indicated by 9 is a CCD camera which is sensitive to the focused light beam provided by the focusing lens 8 and produces an image signal; 10, an operating unit which utilizes the image signal produced from the light of 569-nm wavelength and the image signal produced from the light of 586-nm wavelength thereby to calculate the hemoglobin concentration based on the difference of the signals; 11, a television monitor for displaying the hemoglobin concentration calculated by the operating unit 10; and 12, an image recording device such as a video tape recorder for recording the calculated hemoglobin concentration.

The background of development of the brain activity measuring apparatus will be explained. It has been known long since that brain functions such as the sensory, motor and cognitive functions are borne by different portions of the brain. With the advancement of the cranial neurophysiology and the growing concern in the explication of the information processing mechanism of the central nervous system backed up by the industry, there has arisen a demand of apparatus used for measuring the nervous activity in relation with specific tasks of information processing, localizing the brain functions, and analyzing the roles and interactions among portions of brain in carrying out specific tasks of information processing.

At the surgical resection of temporal lobe for a patient of recurrent epilepsia or the resection of brain tummor, there has been a demand of apparatus used for localizing the brain functions of the brain activity in order to remove abnormal tissue without damaging the important functions of the brain, such the like linguistic function and object recognition. It has been known that there is a correspondence between the hemoglobin concentration and the activity of brain, and accordingly there has been proposed a brain activity measuring apparatus which measures the hemoglobin concentration to indicate the brain activity.

Next, the operation of the brain activity measuring apparatus shown in FIG. 1 will be explained. The light source 2 emits the light toward the brain surface 1. The filter positioner 3 rotates its revolving section 3a to switch the band-pass filters 4 and 5. Accordingly, the light emitted by the light source 2 passes through the filters 4 and 5 alternately, and the light components of wavelengths 586 nm and 569 nm are projected alternately on to the brain surface 1. Shown in FIG. 1 is the illumination of the brain surface 1 by the light component passing through the filter 5. The wavelength of one of the band-pass filters 4 and 5 is selected to match the isosbestic wavelength 569 nm of hemoglobin. In this case, the filter 5 is selected.

The projected light is reflected on the brain surface 1, and the reflected light is received by the objective lens 7 and focused on the CCD camera 9 by the focusing lens 8. The CCD camera 9 produces an image signal of the brain surface 1 from the reflected light of each wavelength individually.

The operating unit 10 inputs image signals of the brain surface 1 produced from the reflected light components of the two wavelengths alternately at predetermined times. The operating unit 10 utilizes the image signal based on 569-nm wavelength and the image signal based on 586-nm wavelength to calculate the hemoglobin concentration, and also to remove background noises included in the image signals.

Background noises include a noise component created by the vibration of the brain surface caused by the heart beat and breathing, for example.

The television monitor 11 displays the hemoglobin concentration calculated by the operating unit 10, and the video tape recorder 12 records the calculated hemoglobin concentration.

The operating unit 10 also calculates the difference between the hemoglobin concentrations when the brain is quiescent and when the brain is stimulated, thereby producing a differential image signal.

Accordingly, the conventional brain activity measuring apparatus is based on the measurement of the hemoglobin concentration which can be used as an index of the brain activity. However, because of the alternate projection of the light components of different wavelengths, there is a time difference between the image signals produced from one reflected light component and the other, and therefore background noises included in the image signals can possibly be different. Under varying background noises, the calculation of the image signals cannot remove the background noises accurately. On this account, the conventional brain activity measuring apparatus is deficient in that in some cases it cannot measure the hemoglobin concentration accurately for use as a signal which indicates the brain activity.

Another problem of the conventional brain activity measuring apparatus is that the mechanical vibration of the filter positioner 3 which turns the filters 4 and 5 creates a noise component in the reflected light, and therefore it cannot measure the hemoglobin concentration accurately for use as a signal which indicates the brain activity.

SUMMARY OF THE INVENTION

The present invention is intended to overcome the foregoing prior art deficiencies, and its prime object is to provide a brain activity measuring apparatus capable of eliminating the creation of a noise component caused by the mechanical vibration of the apparatus, removing background noises accurately, and producing the signal which indicates the brain activity accurately.

Another object of the present invention is to provide a brain activity measuring apparatus capable of clearly displaying portions of brain in connection with the brain activity.

Still another object of the present invention is to provide a brain activity measuring apparatus capable of eliminating the displacement of brain images attributable to the difference of refractivity among various band-pass filters.

Still another object of the present invention is to provide a brain activity measuring apparatus capable of removing background noises accurately thereby to produce a signal which purely indicates the brain activity even in the case of the measurement by staining the brain surface with a voltage-sensitive fluorescent dye.

Still another object of the present invention is to provide a brain activity measuring apparatus which has a simple structure and can be operated easily.

Still another object of the present invention is to provide a brain activity measuring apparatus which operates at an enhanced signal-to-noise ratio.

The brain activity measuring apparatus according to the first aspect of this invention comprises a light path dividing means for splitting and directing the reflected light beam from the brain surface to a plurality of light paths, light transmission means disposed on the light paths and adapted to transmit light components of different wavelengths, and a differential amplifier means which produces a signal of the differential among image signals produced from the light beams which have passed the light transmission means.

This apparatus produces a differential signal of the image signals produced from the light beams which have passed the individual light transmission means, and consequently it can remove background noises accurately. Accordingly, the differential signal purely includes a significant component which exhibits the brain activity. Light components of different wavelengths are produced without using a filter positioner, and accordingly the measurement is free from the influence of the noise component created by the mechanical vibration.

The brain activity measuring apparatus according to the second aspect of this invention comprises a light path dividing means for splitting and directing the reflected light beam from the brain surface to two light paths, light transmission means disposed on the light paths and adapted to transmit light components of different wavelengths, and a differential amplifier means which produces a signal of the difference among image signals produced from the light beams which have passed the light transmission means.

This apparatus produces a differential signal of the two image signals produced from the light beams which have passed the two light transmission means, and consequently it can remove background noises accurately. Accordingly, the differential signal purely includes a significant component which exhibits the brain activity. Light components of different wavelengths are produced without using a filter positioner, and accordingly the measurement is free from the influence of the noise component created by the mechanical vibration.

The brain activity measuring apparatus according to the third aspect of this invention includes intensity adjustment means which equalize the intensity of the background portion of one image signal produced by one image signal producing means and that of another image signal produced by another image signal producing means.

This apparatus operates to measure the brain activity based on the differential signal, with individual image signals being adjusted to have equal intensity, so that the differential amplifier means operates in the operating region of the best signal-to-noise ratio. It prevents the differential signal from taking a negative value, which results in a black image, caused by the subtracting operation for a smaller image signal by a larger image signal.

The brain activity measuring apparatus according to the fourth aspect of this invention includes contrast adjustment means which equalize the contrast of the image signals produced by individual image signal producing means.

Accordingly, this apparatus is capable of suppressing the disparity of brightness in the differential image signals attributable to the difference in color in case the brain surface has multiple colors due to the presence of blood vessels or the like. Consequently, it can clearly display brain portions in connection with the brain activity.

The brain activity measuring apparatus according to the fifth aspect of this invention has its light reception means formed of an objective lens which collimates the reflected light of the light projected by the light projection means, and includes focusing lenses which focus the light beams, which have passed the light transmission means, on the image signal producing means.

Accordingly, this apparatus lets each light transmission means transmit a parallel light beam, preventing the displacement of brain images attributable to the difference of refractivity of individual light transmission means.

The brain activity measuring apparatus according to the sixth aspect of this invention includes correction lenses which correct the brain images produced from the light beams which have passed the light transmission means.

This apparatus lets the correction lenses act on the image formation in the image signal producing means so that the focused images produced from the light beams which have passed the individual light transmission means coincide even in the case of the displacement of images due to the difference of refractivity among the light transmission means. Accordingly, the displacement of images is dissolved, and the apparatus accurately produces a signal which purely indicates the brain activity.

The brain activity measuring apparatus according to the seventh aspect of this invention has its light transmission means formed of thin-film band-pass filters.

Accordingly, this apparatus is free from the displacement of brain images owing to an extremely small thickness of the light transmission means. Consequently it produces a signal which purely indicates the brain activity.

The brain activity measuring apparatus according to the eighth aspect of this invention is intended for the measurement of the brain activity by staining the brain surface with a voltage-sensitive fluorescent dye, and has at least one of its light transmission means formed of a band-pass filter that solely transmits a light component of emission wavelength and at least one of other light transmission means formed of a band-pass filter that solely transmits a light component of excitation wavelength.

Consequently, this apparatus removes background noises accurately even in the case of the measurement of the brain activity by staining the brain surface with a voltage-sensitive fluorescent dye.

The brain activity measuring apparatus according to the ninth aspect of this invention includes a beam splitter which directs by reflection the light projected by the light projection means to the brain surface and directs by transmission the reflected light received by the light reception means to the light path dividing means.

This apparatus can have its light projection means and light reception means formed as an integrated member, and accordingly the apparatus has a simple structure and can be operated easily.

The brain activity measuring apparatus according to the tenth aspect of this invention has its light path dividing means formed of a beam splitter which reflects a light component having a certain wavelength in the reflected light from the brain surface and transmits the other light component having another wavelength.

This apparatus splits and directs the reflected light to multiple light paths without diminishing the intensity of the reflected light, and consequently it operates at an improved signal-to-noise ratio and produces a signal which purely indicates the brain activity.

DESCRIPTION OF THE PREFERRED EMBODIMENTS

Embodiment 1

Figure 1:
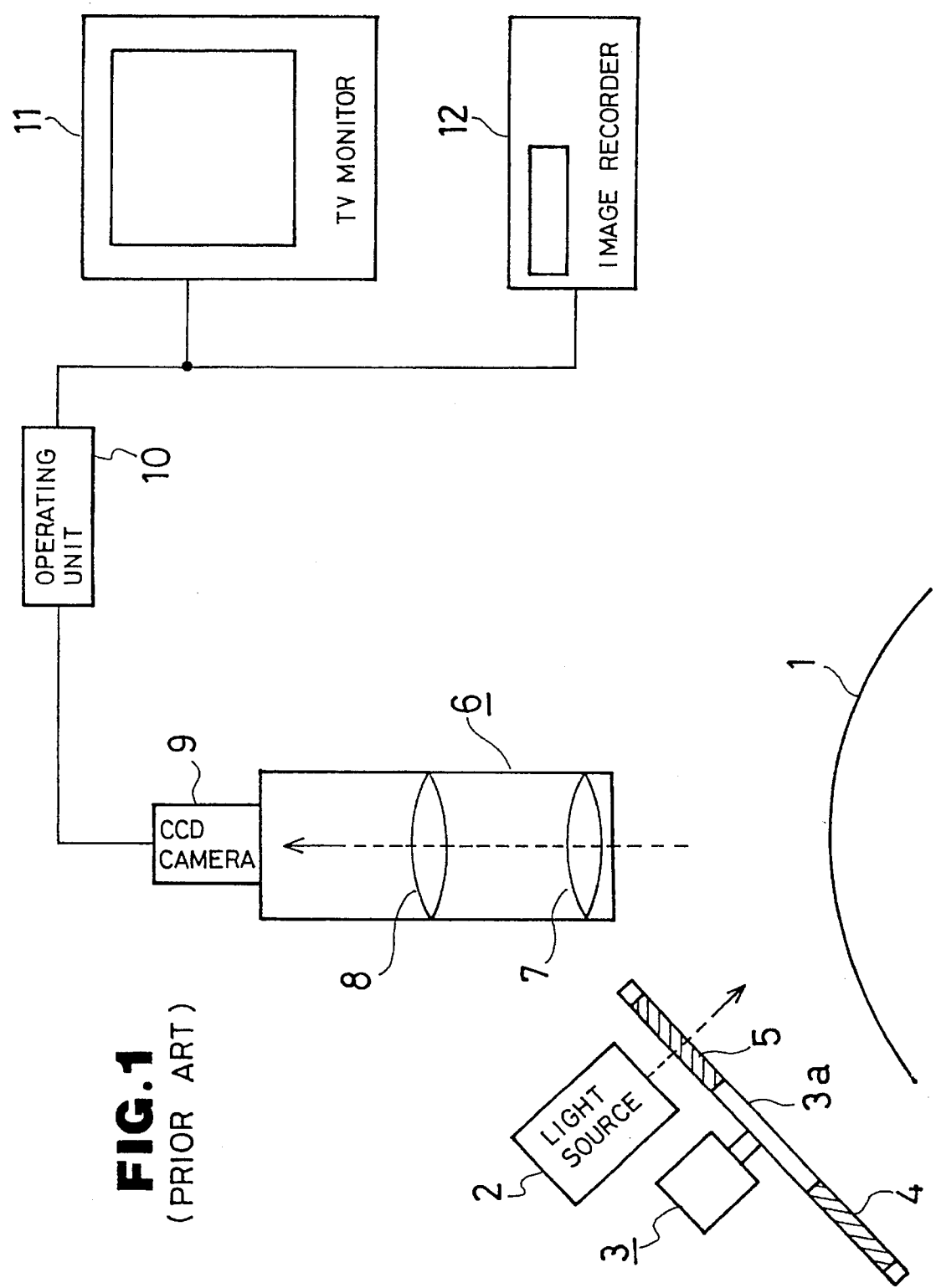
FIG. 1 is a diagram showing the arrangement of the conventional brain activity measuring apparatus.
Figure 2:
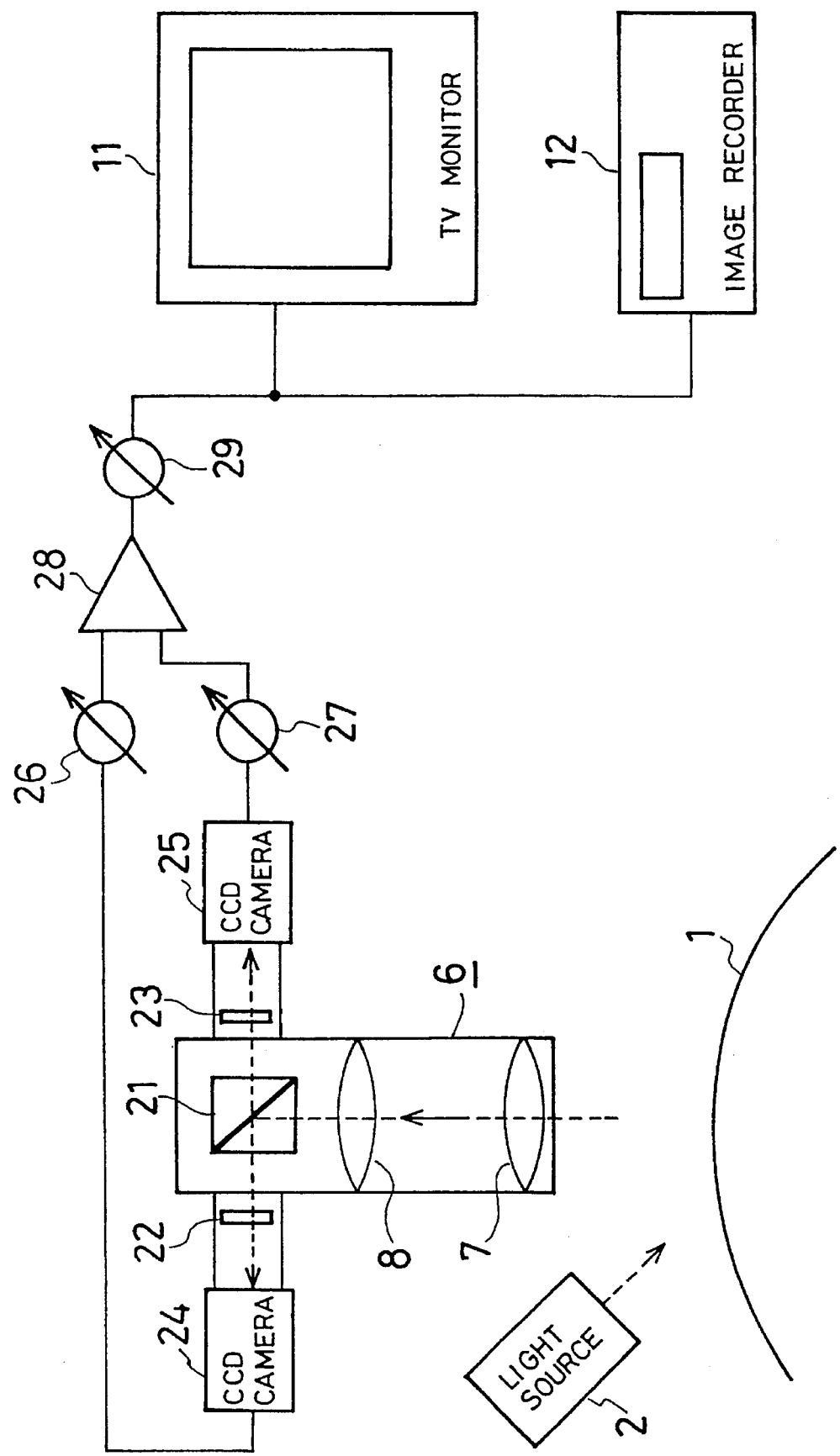
FIG. 2 is a diagram showing the brain activity measuring apparatus based on a first embodiment of this invention.

FIG. 2 shows the arrangement of the brain activity measuring apparatus based on the first embodiment of this invention. Reference numeral 1 denotes the brain surface of an animal including human, 2 is a light source which produces and projects a ray of light on to the brain surface 1, and 6 is a lens barrel, in which are fitted an objective lens 7 and a focusing lens 8 for focusing the reflected light from the brain surface 1. The objective lens 7 and focusing lens 8 constitute the light reception means. Indicated by 21 is a beam splitter which splits the reflected light beam focused by the focusing lens 8 into two light beams, 22 and 23 are optical band-pass filters which are disposed on the light paths from the beam splitter 21 and adapted to transmit light components of different frequency bands, and 24 and 25 are CCD cameras which are sensitive to the light beams passing through the filters 22 and 23, respectively, and produce respective image signals.

Indicated by 26 and 27 are gain adjustment devices which are used to equalize the intensity of the image signals produced by the CCD cameras 24 and 25, respectively, 28 is a differential amplifier which evaluates at the resolution of pixel the difference of the image signals released by the gain adjustment devices 26 and 27 and produces a differential signal, and 29 is a gain adjustment device which adjusts the amplitude of the differential signal produced by the differential amplifier 28.

Next, the operation of the apparatus will be explained. The light source 2 projects the light on to the brain surface 1. The reflected light from the brain surface 1 is received by the objective lens 7, and split and directed on to two light paths by the beam splitter 21, and the two light beams are incident to the band-pass filters 22 and 23 disposed on the light paths.

The band-pass filters 22 and 23 transmit only the light components of certain wavelength ranges. Accordingly, only the light components with the wavelength ranges out of the reflected light having a wide spectrum are focused on the CCD cameras 24 and 25. In the case of measuring the hemoglobin concentration as a signal which exhibits: the brain activity, the filters 22 and 23 which transmit only light components of wavelengths around 570 nm and 630 nm, respectively, are used.

The CCD cameras 24 and 25 produce image signals of the brain surface 1 from the focused reflected light. The image signals are rendered the intensity adjustment by the respective gain adjustment devices 26 and 27, and then fed to the differential amplifier 28.

The differential amplifier 28 implements the differential calculation for the image signals at the resolution of pixel by subtracting the image signal provided by the gain adjustment device 27 from the image signal provided by the gain adjustment device 26, thereby producing a differential signal. The image signal based on the light of 570-nm wavelength consists of a significant component which exhibits the brain activity and a background noise component, while the image signal based on 630-nm wavelength consists of only the background noise component. Accordingly, by subtracting the image signal of 630-nm wavelength from that of 570-nm wavelength, the background noise component is removed and the signal which exhibits the brain activity is extracted.

Figure 3:
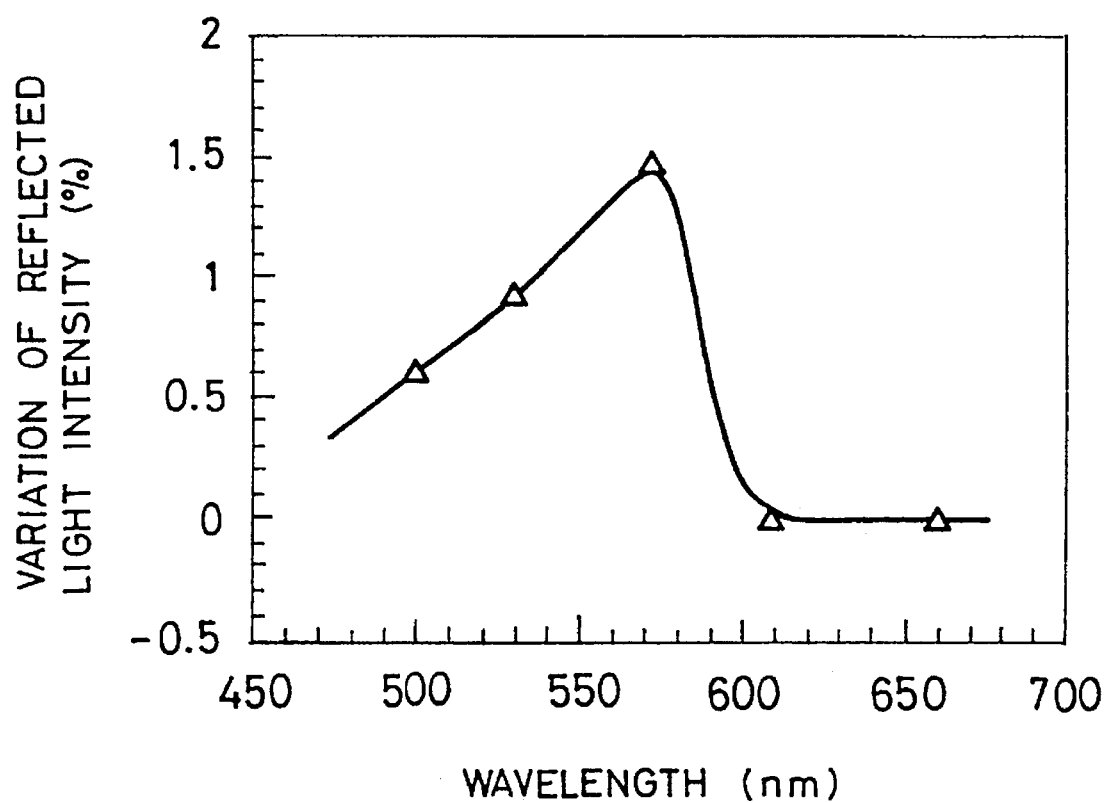
FIG. 3 is a graph showing the relationship between the variation of intensity of the image signal and the wavelength of reflected light.

This embodiment will be explained more specifically. One of physiological values which can be used as an index of the brain activity is the hemoglobin concentration, as mentioned previously. In this case, as shown in FIG. 3, when the light with a wavelength around 570 nm (560–580 nm) is projected on to the brain surface, the reflected light has a very large intensity change in connection with the brain activity relative to the quiescent state of the brain, in contrast to the projection of the light with a wavelength around 630 nm (610–650 nm) in which case the intensity change is very small. Specifically, the light of 570-nm wavelength produces an intensity change of 1.5%, whereas that of 630-nm wavelength produces only 0.1% intensity variation.

The image signal produced from the reflected light of around 570-nm wavelength changes largely and includes a significant component that exhibits the brain activity, whereas the image signal produced from the reflected light of around 630-nm wavelength changes little and is almost only a background noise component. Accordingly, by calculating the difference of the two image signals, the background noise component is removed and a signal which purely exhibits the brain activity can be obtained.

The gain adjustment device 29 adjusts the amplitude of the differential signal produced by the differential amplifier 28, and delivers the resulting signal to the television monitor 11 and video tape recorder 12. The television monitor 11 displays the hemoglobin concentration in terms of the image of brain activity based on the differential signal, and the video tape recorder 12 records the signal of hemoglobin concentration.

The above process provides an image according to the hemoglobin concentration reflecting the brain activity. It is also possible for the apparatus to calculate the difference between the hemoglobin concentrations when the brain is quiescent and when the brain is stimulated, thereby producing a differential image signal, as in the case of the conventional apparatus.

The reason for the adjustment of the intensity level of the crude image signals by the gain adjustment devices 26 and 27 will be briefed. If the sensitivities of the CCD cameras 24 and 25 are not balanced properly, i.e., if the CCD camera 24 produces an image signal of lower intensity level than that of the CCD camera 25, the result of subtraction of the signals will be negative and the hemoglobin concentration cannot be evaluated from the differential signal. On this account, adjustment is made in advance with the gain adjustment devices 26 and 27 such that both CCD cameras 24 and 25 produce image signals of equal intensity level for a same object.

Embodiment 2

Figure 4:
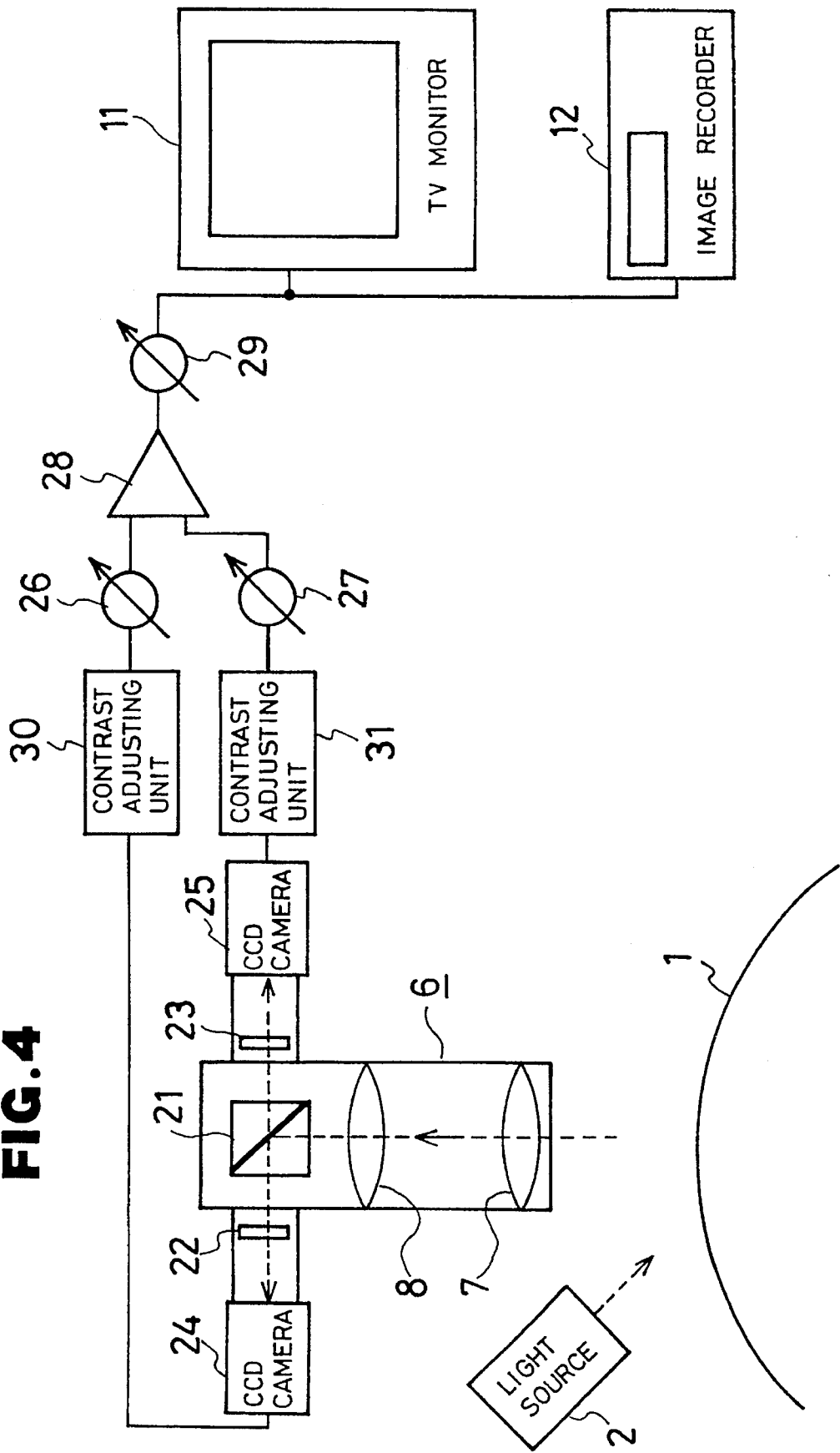
FIG. 4 is a diagram showing the brain activity measuring apparatus based on a second embodiment of this invention.

FIG. 4 shows the brain activity measuring apparatus based on the second embodiment of this invention. The apparatus includes contrast adjustment units 30 and 31, which are used to equalize the contrast of the image signals provided by the CCD cameras 24 and 25.

The operation of the contrast adjustment units 30 and 31, which is only different portion of operation from the first embodiment, will be explained. The apparatus includes contrast adjustment units 30 and 31, which are used to equalize the contrast of the image signals provided by the CCD cameras 24 and 25 based on the y-correction or the like. The reason for equalizing the contrast of both image signals is as follows.

The CCD cameras 24 and 25 have the formation of images based on light components of different wavelengths, and therefore the image signals can have different contrast attributable to multiple colors of the brain surface due to the existence of blood vessels and the like.

For example, in case the filter 22 has a higher transmittance of red and a lower transmittance of green than the filter 23, the image signal produced by the CCD camera 24 has an intensified red component and a weakened green component relative to the image signal produced by the CCD camera 25, and the difference of contrasts with and without blood vessels in one image signal will be different from the difference in the other image signal.

When the image signals are rendered the differential processing, with their contrasts being left different, the background sections of the signals cannot be made equal at the portions of different contrasts. In order to extract a signal which purely exhibits the brain activity, the contrast adjustment units 30 and 31 are used to equalize the contrast of the image signals produced by the CCD cameras 24 and 25 so that the whole differential image signal has a unique attribute of color.

Alternatively, the CCD cameras 24 and 25 may be provided with a contrast adjustment function, instead of using the contrast adjustment units 30 and 31.

Embodiment 3

Figure 5:
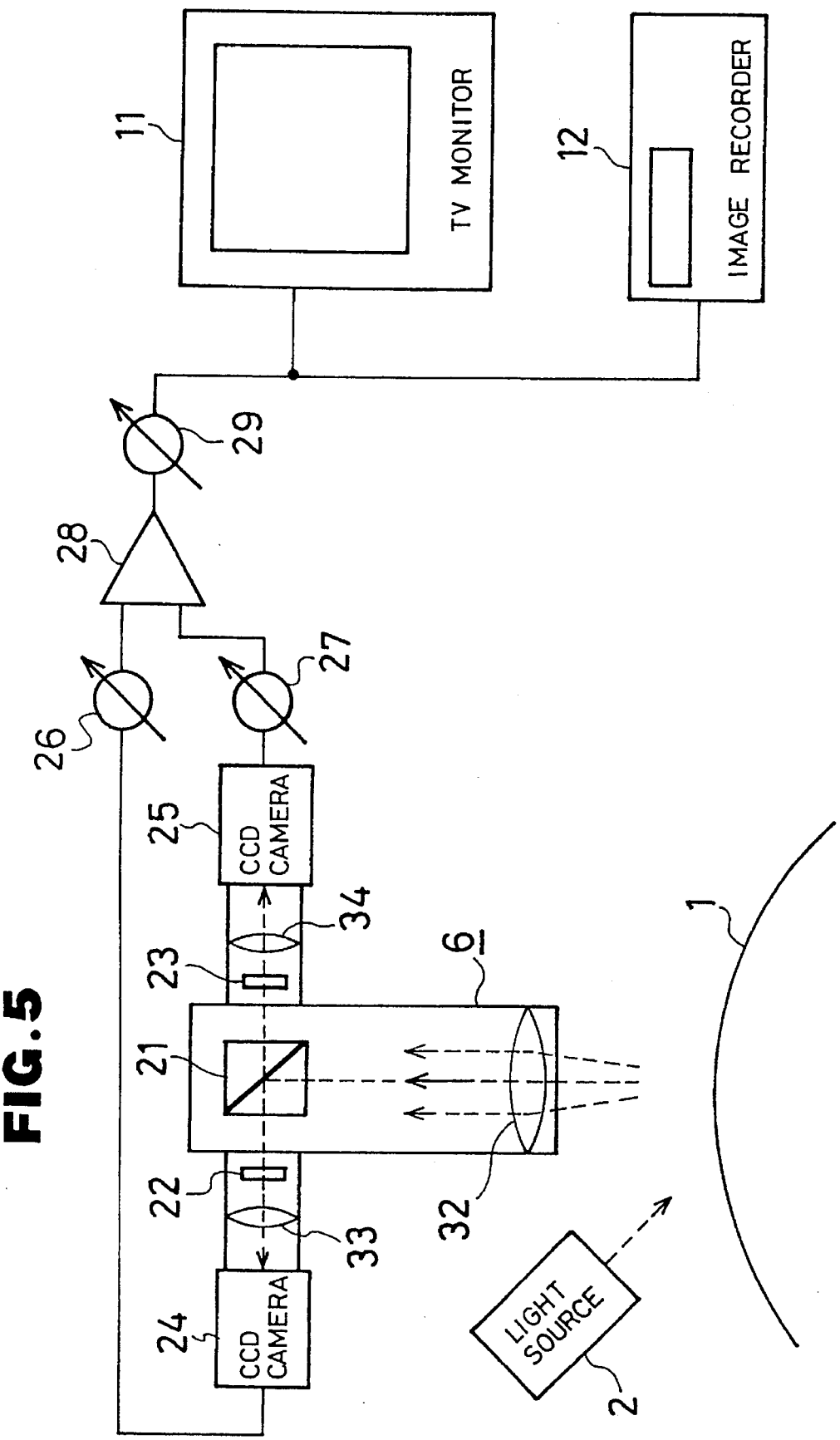
FIG. 5 is a diagram showing the brain activity measuring apparatus based on a third embodiment of this invention.

In the first embodiment; light reception means consists of the objective lens 7 and focusing lens 8. However, such a brain activity measuring apparatus is available as the light reception means consists of an objective lens 32 which forms the reflected light into a parallel light beam and focusing lenses 33 and 34 are used to focus the light beams, which have passed the band-pass filters 22 and 23, on the CCD cameras 24 and 25, as shown in FIG. 5.

In the first embodiment, in which the light reception means consists of the objective lens 7 and focusing lens 8 and the reflected light beam focused by the focusing lens 8 is split and incident to the band-pass filters 22 and 23, the split light beams are refracted by the filters 22 and 23 depending on their refractivities, resulting possibly in the disparity of focal points and then resulting magnifications. Whereas, according to this embodiment, the parallel light beam from the objective lens 32 is split and incident to the band-pass filters 22 and 23, and accordingly the reflected light beams are prevented from being refracted and having their focal points shifted. Consequently, the apparatus of this embodiment produces the differential signal which exhibits the brain activity more accurately as compared with the first embodiment.

Embodiment 4

Figure 6:
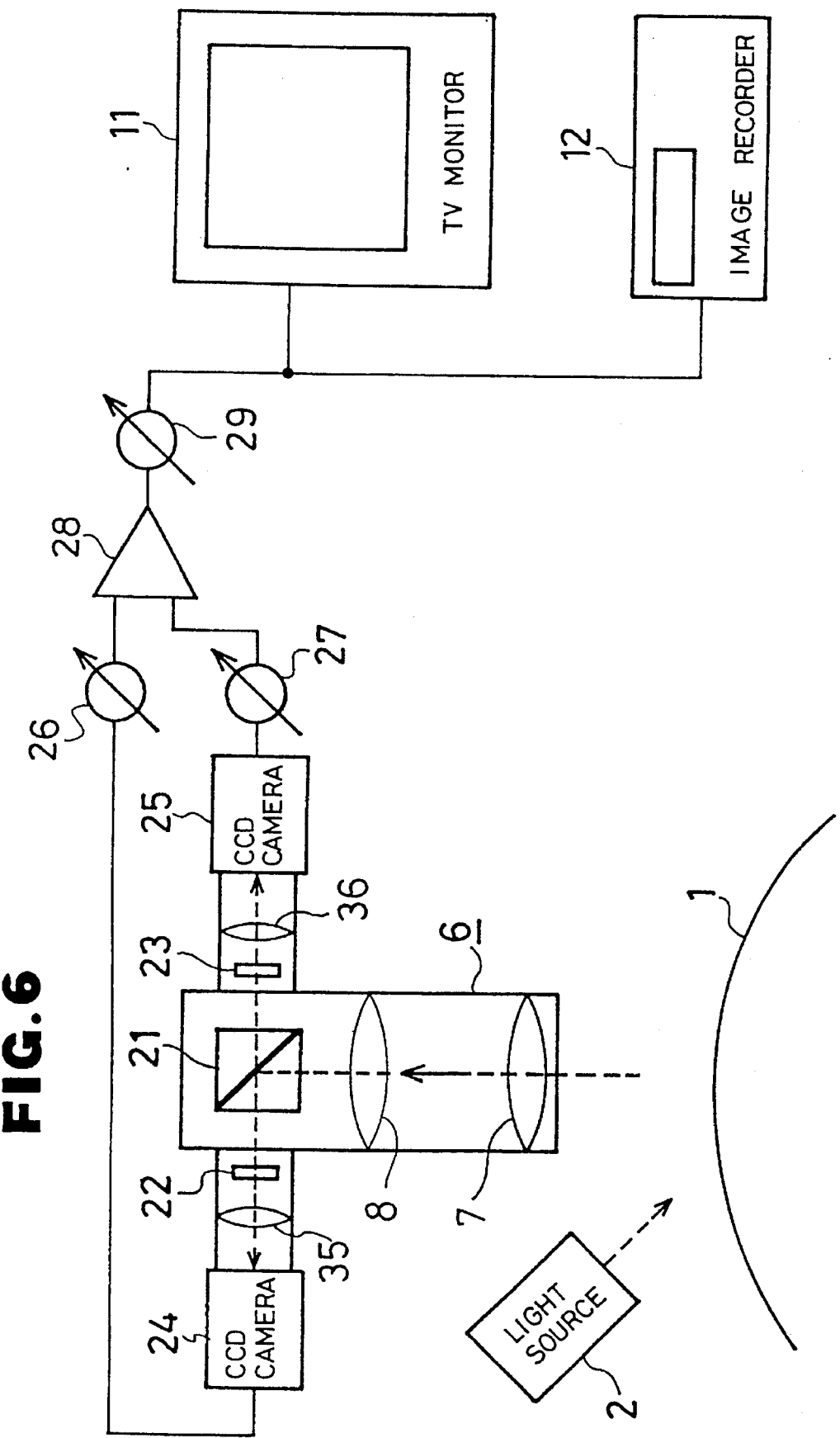
FIG. 6 is a diagram showing the brain activity measuring apparatus based on a fourth embodiment of this invention.

Although in the third embodiment the light reception means consists of the objective lens 32 and the focusing lenses 33 and 34 are disposed behind of the band-pass filters 22 and 23, FIG. 6 shows a brain activity measuring apparatus which has basically the arrangement shown in FIG. 2 and additionally has correction lenses 35 and 36 for correcting the images of the light beams which have passed the band-pass filters 22 and 23. In this case, the same effect as the third embodiment can be obtained.

The correction lenses 35 and 36 are disposed on the output side of the filters 22 and 23 with the intention of correcting the disparity of focal points attributable to the difference of refractivity of the filters, which is the case of the first embodiment described previously. The correction lenses 35 and 36 function to equalize the focal points on the CDD cameras 24 and 25 of the light beams which have passed the filters 22 and 23. Consequently, the apparatus of this embodiment produces the differential signal which exhibits the brain activity accurately as in the case of the third embodiment.

Alternatively, the outputs of the CCD cameras 24 and 25 may be corrected electrically, instead of using the correction lenses 35 and 36.

Embodiment 5

Figure 7:
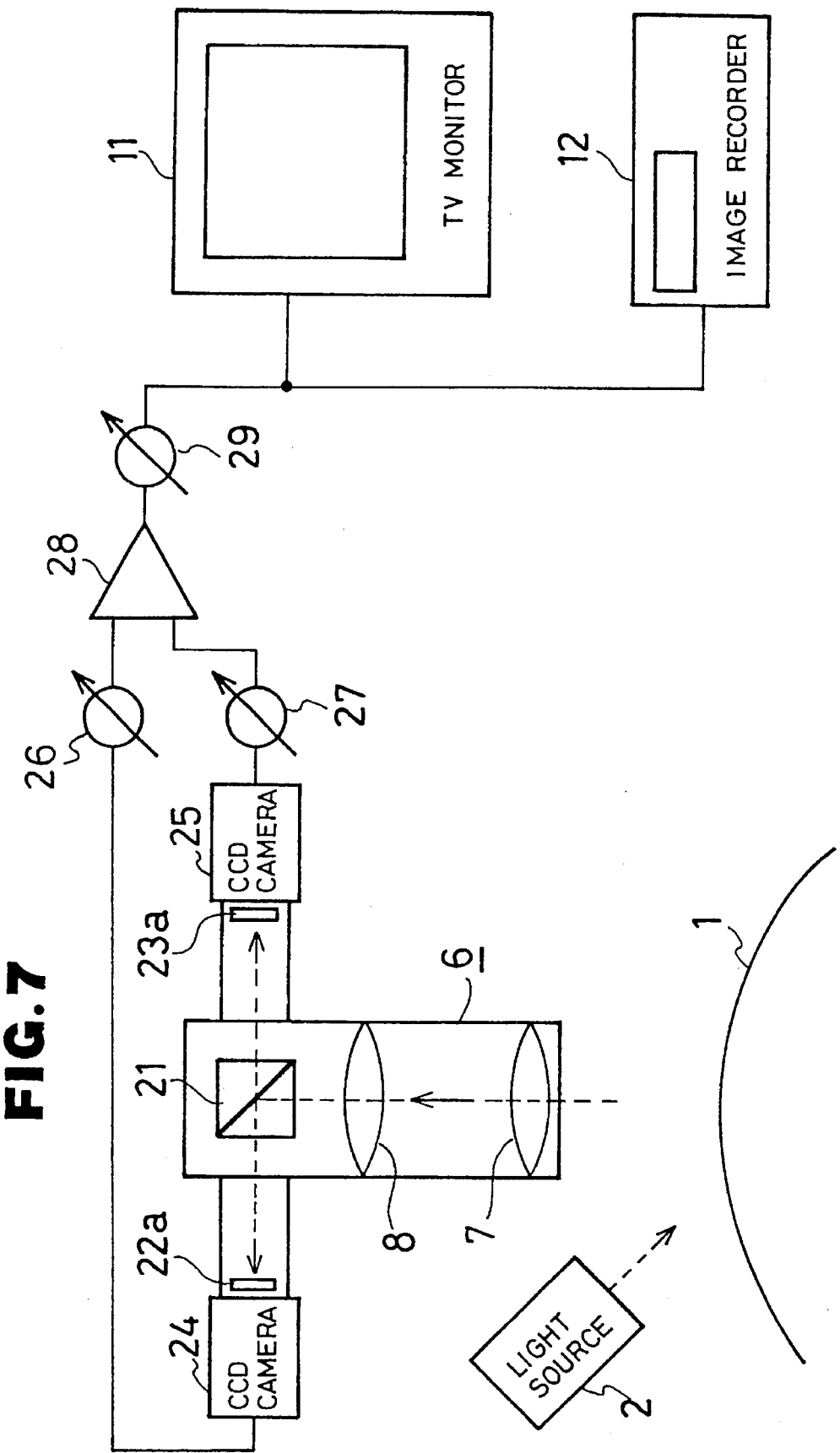
FIG. 7 is a diagram showing the brain activity measuring apparatus based on a fifth embodiment of this invention.

Although in the third embodiment the light reception means consists of the objective lens 32 and the focusing lenses 33 and 34 are disposed behind of the band-pass filters 22 and 23, FIG. 7 shows a brain activity measuring apparatus having band-pass filters 22a and 23a made of thin-film, in place of the band-pass filters 22 and 23 of the first embodiment. In this case, the same effect as the third embodiment can be obtained.

The difference in the degree of refraction attributable to the difference of refractivity of band-pass filters is proportional to the thickness of the filters. By using the thin-film band-pass filters 22a and 23a, the refraction of the reflected light beams is made negligibly small, and the disparity of focal points can be prevented.

Embodiment 6

In the case of measuring the brain activity by staining the brain surface with a voltage-sensitive fluorescent dye, e.g., N-(3-dimethylethanol ammonium-2-hydroxypropyl)-4-(4-P-diethylaminopheny) 1', 3'-butadienylpyridium acetate), a brain activity measuring apparatus includes a band-pass filter 22 which transmits only a light component of emission wavelength of fluorescence and a band-pass filter 23 which transmits only a light component of excitation wavelength.

The reflected light with the emission wavelength of fluorescence includes both of a significant component which exhibits the brain activity and a background noise component, while the reflected light of excitation wavelength includes only the background noise component. Accordingly, by calculating the difference of the two image signals produced from these light beams, the background noise component is removed and a signal which purely exhibits the brain activity can be obtained.

Embodiment 7

Figure 8:
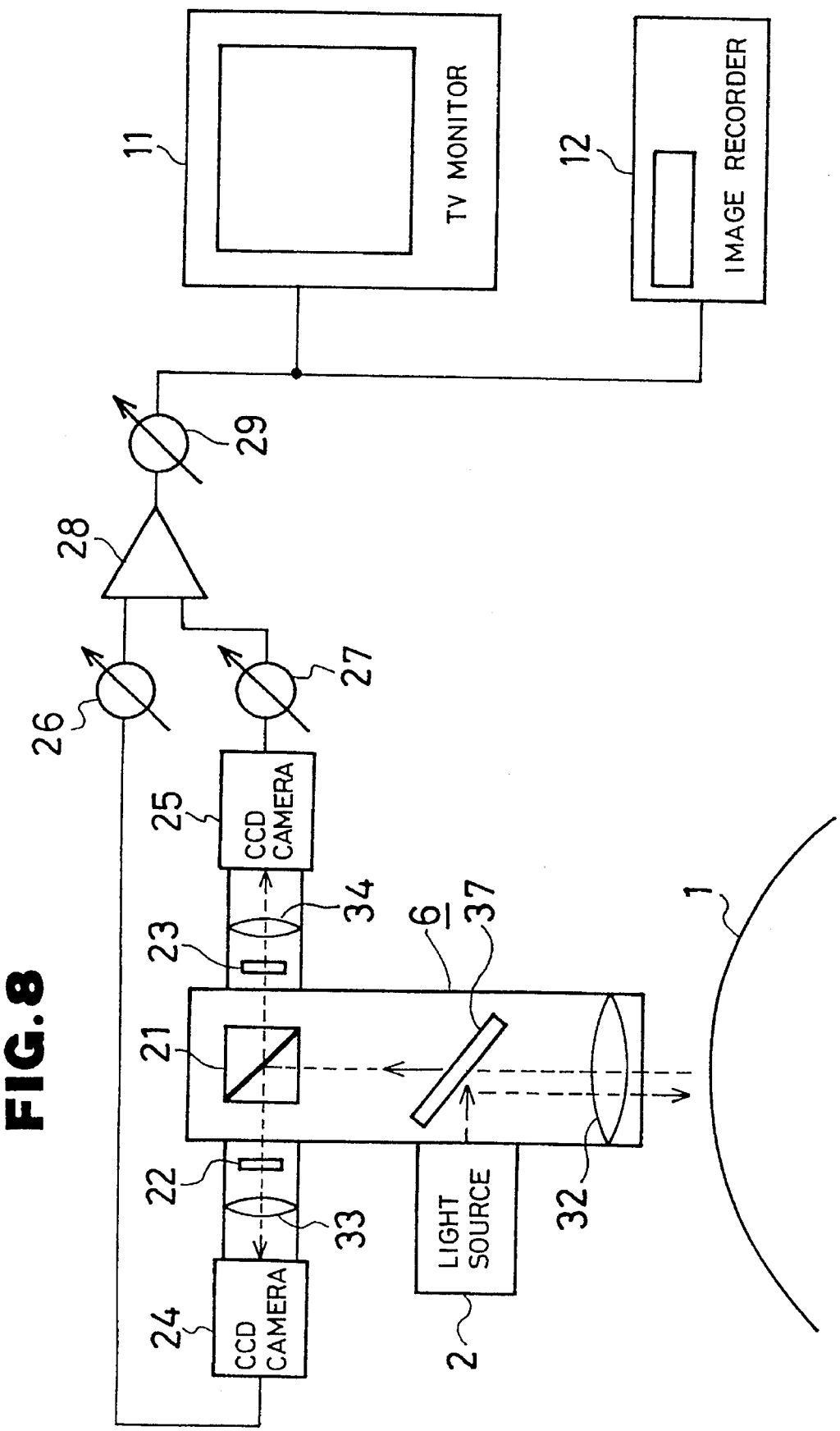
FIG. 8 is a diagram showing the brain activity measuring apparatus based on a sixth embodiment of this invention.

FIG. 8 shows a brain activity measuring apparatus having a beam splitter 37 formed of a dichroic mirror or the like which directs by reflection a ray of light emitted by the light source 2 to the brain surface 1 and directs by transmission the reflected light from the objective lens 32 to the beam splitter 21. The light source 2 and the lens barrel 6 can be integrated, in contrast to the preceding embodiments in which the light source 2 and lens barrel 6 are separated. Consequently, the apparatus of this embodiment has a simple structure and can be operated easily.

Embodiment 8

Figure 9:
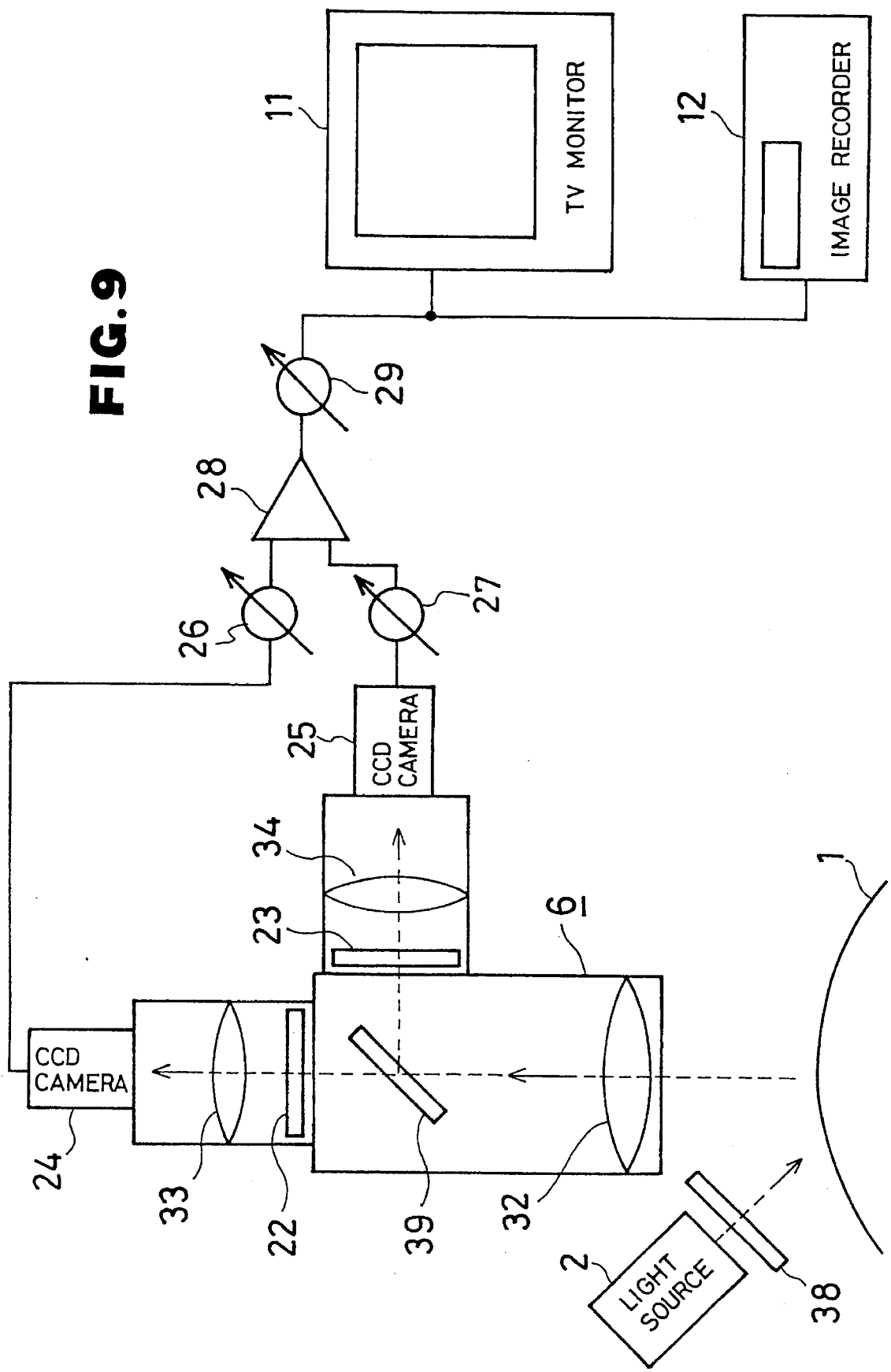
FIG. 9 is a diagram showing the brain activity measuring apparatus based on a eighth embodiment of this invention.

FIG. 9 shows a brain activity measuring apparatus having an excitation band-pass filter 38 disposed at the output of the light source 2 and a beam splitter 39 formed of a dichroic mirror or the like which splits and directs by reflection or by transmission depending on the wavelength the reflected light from the objective lens 32 to two light paths, in contrast to the preceding embodiments in which the beam splitter 21 splits the reflected light.

The beam splitter 39 such as a dichroic mirror functions to transmit light components of wavelengths longer than a certain threshold and reflect light components of wavelengths shorter than the threshold, or transmit light components of wavelengths shorter than a certain threshold and reflect light components of wavelengths longer than the threshold. Accordingly, it can split and direct the reflected light to two light paths, thereby achieving the same function as the beam splitter 21 used in the preceding embodiments.

Furthermore, a dichroic mirror divides the light path depending on the wavelength of the inputting reflected light, with an advantage of dividing the light path without diminishing the light intensity of each wavelength required for producing each image signal. The beam splitter 21 of the preceding embodiments simply splits the inputting reflected light into two equal light beams irrespective of the wavelength, and therefore the intensity of the light which is incident to each CCD camera, and thus the, light component of the wavelength necessary to produce each image signal decreases to a half of the crude reflected light from the brain surface 1. Accordingly, the light intensity necessary for producing each image signal is decreased to a half. As a result, a signal-to-noise ratio is deteriorated, thus leading to a possibility of an adverse influence on measuring accuracy of a signal reflecting the brain activity. Whereas, the use of the dichroic mirror according to this embodiment is advantageous in that it divides the light path depending on the wavelength of the inputting reflected light and accordingly it does not diminish the light intensity of each wavelength necessary for producing each image signal. Consequently, the apparatus of this embodiment operates at an improved signal-to-noise ratio to produce a signal which exhibits the brain activity more accurately.

Although this embodiment bases the splitting of light on three band-pass filters 22, 23 and 38, it is also possible to split the reflected light into two beams of prescribed wavelengths by using only a dichroic mirror.

Embodiment 9

Figure 10:
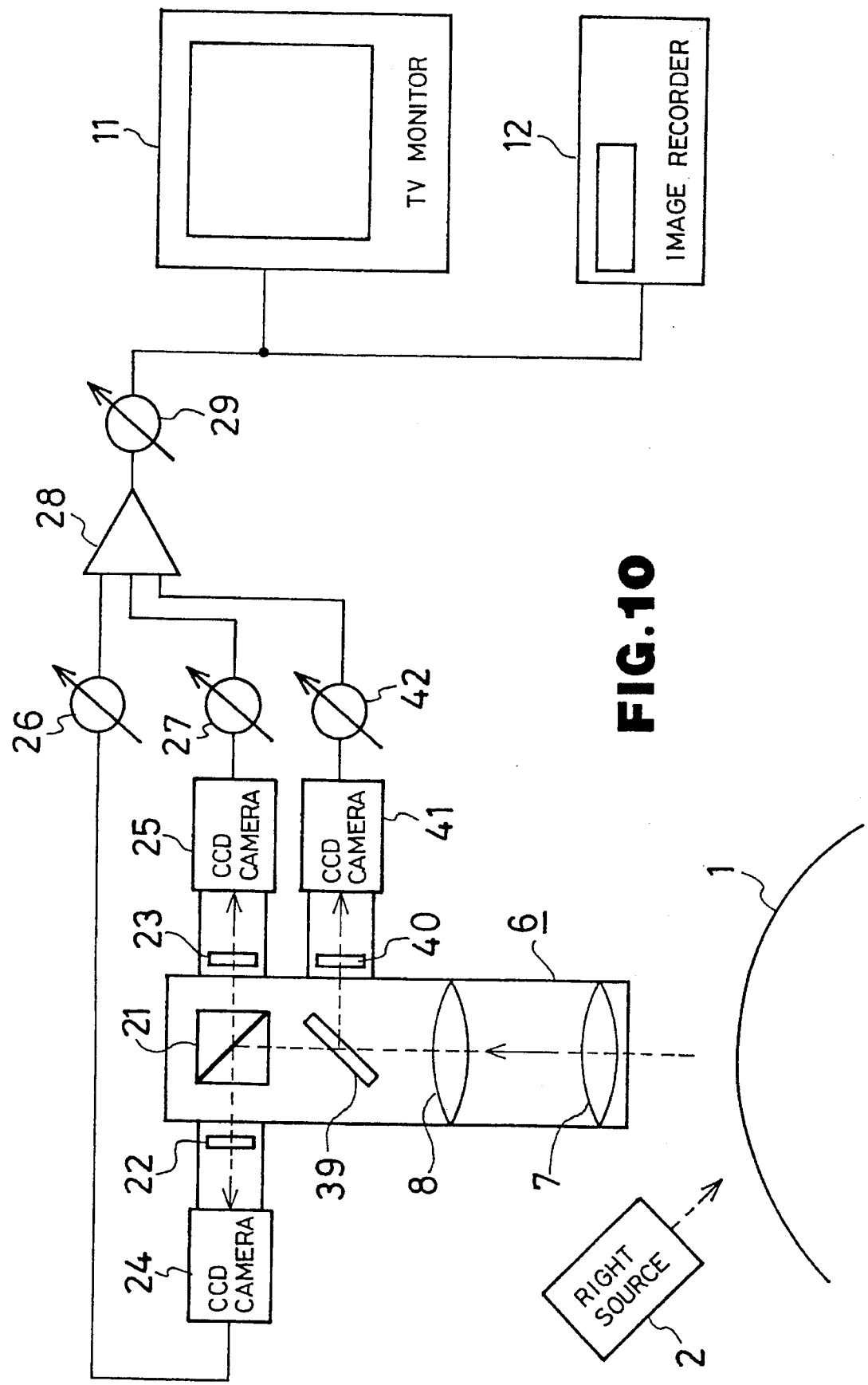
FIG. 10 is a diagram showing the brain activity measuring apparatus based on a ninth embodiment of this invention.

FIG. 10 shows a brain activity measuring apparatus having a dichroic mirror 39 and beam splitter 21 to split and direct the reflected light to three light paths, in contrast to the preceding embodiments having two divided light paths. The apparatus includes an additional. band-pass filter 40, CCD camera 41 and gain adjustment device 42.

Although the foregoing embodiments all employ CCD cameras as a means of image signal formation, an array or arrays of photodiodes having a large signal-to-noise ratio may be used instead.

Although the foregoing embodiments all employ gain adjustment devices has a means of electrical intensity adjustment, optical diaphragms may be used instead.

What is claimed is:

1. A brain activity measuring apparatus comprising:

light projection means for projecting a ray of light on to a surface of a brain;

light reception means for receiving a reflected light, which is derived from the projected light, from the brain surface;

light path dividing means for splitting and directing a light beam provided by said light reception means to a plurality of light paths;

light transmission means disposed on said light paths and adapted to transmit light beams having light components of different wavelengths;

image signal producing means for producing image signals from the light beams transmitted by said light transmission means; and differential amplifier means for producing a differential signal based on a difference of the image signals produced by said image signal producing means.

2. A brain activity measuring apparatus according to claim 1, wherein said light path dividing means splits and directs the light beam to two light paths.

3. A brain activity measuring apparatus according to claim 2 further including intensity adjustment means for equalizing the intensity of a background section of the image signal produced by one image signal producing means and the intensity of the background section of another image signal produced by another image signal producing means.

4. A brain activity measuring apparatus according to claim 2 further including contrast adjustment means for equalizing the contrast of the image signals produced by said image signal producing means.

5. A brain activity measuring apparatus according to claim 2, wherein said light reception means comprises an objective lens which forms the reflected light into a parallel light beam, and wherein said apparatus further includes focusing lenses for focusing the light beams, which have passed said light transmission means, on said image signal producing means.

6. A brain activity measuring apparatus according to claim 2 further including correction means for correcting the light beams, transmitted by said light transmission means, so as to equalize a focal point of each of the light beams on the image signal producing means.

7. A brain activity measuring apparatus according to claim 2, wherein said light transmission means comprises band-pass filters of thin film.

8. A brain activity measuring apparatus according to claim 2, wherein at least one of said light transmission means is a band-pass filter which transmits only a light component of emission wavelength and at least one of other light transmission means is a band-pass filter which transmits only a light component of excitation wavelength.

9. A brain activity measuring apparatus according to claim 2 including a beam splitter which directs based on reflection the light produced by said light projection means to the brain surface and directs based on transmission the reflected light received by said light reception means to said light path dividing means..

10. A brain activity measuring apparatus according to claim 2, wherein said light path dividing means includes a beam splitter which reflects a light component of one particular wavelength in the reflected light and transmits another light component of another particular wavelength in the reflected light.

11. A brain activity measuring apparatus according to claim 2, wherein the light transmission means includes first and second light transmission means each respectively receiving one of the two light paths wherein said first light transmission means transmits a light component having wavelengths of approximately 570 nm and said second light transmission means transmits a light component having wavelengths of approximately 630 nm.

12. A brain activity measuring apparatus according to claim 1 further including intensity adjustment means for equalizing the intensity of a background section of the image signal produced by one image signal producing means and the intensity of the background section of other image signals produced by another image signal producing means.

13. A brain activity measuring apparatus according to claim 12, wherein said light reception means comprises an objective lens which forms the reflected light into a parallel light beam, and wherein said apparatus further includes focusing lenses for focusing the light beams, which have passed said light transmission means, on said image signal producing means.

14. A brain activity measuring apparatus according to claim 12 further including correction means for correcting the light beams, transmitted by said light transmission means, so as to equalize a focal point of each of the light beams on the image signal producing means.

15. A brain activity measuring apparatus according to claim 12, wherein said light transmission means comprises band-pass filters of thin film.

16. A brain activity measuring apparatus according to claim 12, wherein at least one of said light transmission means is a band-pass filter which transmits only a light component of emission wavelength and at least one of other light transmission means is a band-pass filter which transmits only a light component of excitation wavelength.

17. A brain activity measuring apparatus according to claim 12 including a beam splitter which directs based on reflection the light produced by said light projection means to the brain surface and directs based on transmission the reflected light received by said light reception means to said light path dividing means.

18. A brain activity measuring apparatus according to claim 12, wherein said light path dividing means includes a beam splitter which reflects a light component of one particular wavelength in the reflected light and transmits another light component of another particular wavelength in the reflected light.

19. A brain activity measuring apparatus according to claim 1 further including contrast adjustment means for equalizing the contrast of the image signals produced by said image signal producing means.

20. A brain activity measuring apparatus according to claim 19, wherein said light reception means comprises an objective lens which forms the reflected light into a parallel light beam, and wherein said apparatus further includes focusing lenses for focusing the light beams, which have passed said light transmission means, on said image signal producing means.

21. A brain activity measuring apparatus according to claim 19 further including correction means for correcting the light beams, transmitted by said light transmission means, so as to equalize a focal point of each of the light beams on the image signal producing means.

22. A brain activity measuring apparatus according to claim 19, wherein said light transmission means comprises band-pass filters of thin film.

23. A brain activity measuring apparatus according to claim 19, wherein at least one of said light transmission means is a band-pass filter which transmits only a light component of emission wavelength and at least one of other light transmission means is a band-pass filter which transmits only a light component of excitation wavelength.

24. A brain activity measuring apparatus according to claim 19 including a beam splitter which directs based on reflection the light produced by said light projection means to the brain surface and directs based on transmission the reflected light received by said light reception means to said light path dividing means.

25. A brain activity measuring apparatus according to claim 19, wherein said light path dividing means includes a beam splitter which reflects a light component of one particular wavelength in the reflected light and transmits another light component of another particular wavelength in the reflected light.

26. A brain activity measuring apparatus according to claim 1, wherein said light reception means comprises an objective lens which forms the reflected light into a parallel light beam, said apparatus further includes focusing lenses for focusing the light beams, which have passed said light transmission means, on said image signal producing means.

27. A brain activity measuring apparatus according to claim 1 further including correction means for correcting the light beams, transmitted by said light transmission means, so as to equalize a focal point of each of the light beams on the image signal producing means.

28. A brain activity measuring apparatus according to claim 1, wherein said light transmission means comprises band-pass filters of thin film.

29. A brain activity measuring apparatus according to claim 1, wherein at least one of said light transmission means is a band-pass filter which transmits only a light component of emission wavelength and at least one of other light transmission means is a band-pass filter which transmits only a light component of excitation wavelength.

30. A brain activity measuring apparatus according to claim 1 including a beam splitter which directs based on reflection the light produced by said light projection means to the brain surface and directs based on transmission the reflected light received by said light reception means to said light path dividing means.

31. A brain activity measuring apparatus according to claim 1, wherein said light path dividing means includes a beam splitter which reflects a light component of one particular wavelength in the reflected light and transmits another light component of another particular wavelength in the reflected light.

32. A brain activity measuring apparatus comprising:
   a light source;
   a lens barrel which receives light reflected off of a surface of a brain from said light source and splits said received light into at least two beams of light;
   a plurality of filters each associated with a corresponding beam of light, each filter passing a different range of predetermined wavelengths;
   a plurality of image signal producers each associated with a corresponding filter; and
   a differential amplifier which receives image signals produced by each image signal producer, evaluates a difference of the image signals and produces a differential signal representative of relative brain activity.

33. A method of measuring brain activity, comprising the steps of:
   projecting light towards a surface of a brain;
   splitting light reflected off the surface of the brain into a plurality of light beams;
   filtering each light beam of the plurality of light beams to generate a plurality of filtered light beams, each filtered light beam having different wavelength components than other filtered light beams of the plurality of filtered light beams;
   producing a plurality of image signals, each image signal of the plurality of image signals corresponding to one filtered light beam of the plurality of filtered light beams; and
   producing a differential signal representative of relative brain activity using the plurality of image signals.

* * * * *